United States Patent [19]

Fisher et al.

[11] 4,228,154

[45] Oct. 14, 1980

[54] PURIFICATION OF PLASMA ALBUMIN BY ION EXCHANGE CHROMATOGRAPHY

[75] Inventors: Joseph D. Fisher, Chicago Heights; Willie M. Curry; Michael E. Hrinda, both of Park Forest, all of Ill.

[73] Assignee: Armour Pharmaceutical Company, Scottsdale, Ariz.

[21] Appl. No.: 14,837

[22] Filed: Feb. 26, 1979

[51] Int. Cl.$^2$ .................. A61K 37/02; C07G 7/00
[52] U.S. Cl. .................. 424/101; 260/122; 424/177
[58] Field of Search .................. 260/122; 424/101, 177

[56] References Cited

U.S. PATENT DOCUMENTS

| | | | |
|---|---|---|---|
| 3,497,492 | 2/1970 | Buck et al. | 260/122 |
| 3,686,395 | 8/1972 | Stephan | 424/101 |
| 3,916,026 | 10/1975 | Stephan | 424/177 |
| 3,992,367 | 11/1976 | Plan et al. | 260/122 |
| 3,998,946 | 12/1976 | Condie et al. | 424/101 |
| 4,081,431 | 3/1978 | Stephan et al. | 260/112 B |
| 4,086,222 | 4/1978 | Lindquist et al. | 260/122 |
| 4,094,965 | 6/1978 | Layne et al. | 260/122 X |
| 4,096,136 | 6/1978 | Ayers et al. | 260/112 B |
| 4,136,094 | 1/1979 | Condie | 260/122 |

OTHER PUBLICATIONS

Vox Sang., 33, pp. 97–107, Curling et al., 1977.

*Primary Examiner*—Howard E. Schain
*Attorney, Agent, or Firm*—Merriam, Marshall & Bicknell

[57] ABSTRACT

Purified plasma albumin is obtained by ion exchange chromatographic procedures and in the absence of process steps involving precipitation or desorption of the albumin.

11 Claims, No Drawings

PURIFICATION OF PLASMA ALBUMIN BY ION EXCHANGE CHROMATOGRAPHY

BACKGROUND

The present invention relates generally to purification of proteinaceous substances and more particularly to isolation of plasma albumin by means of ion exchange chromatographic procedures.

Among the more abundant and therapeutically significant proteinaceous materials in blood plasma is albumin. This material is present, for example, in human blood plasma at a concentration of approximately 35 to 55 grams per liter. As is the case with other biological fluids, blood plasma is most commonly fractionated—and albumin is most commonly isolated from among 30 or more other plasma proteins—by methods based on differential solubility of component proteins in aqueous and aqueous-organic solvent systems. The predominant plasma fractionation procedure presently employed for isolation of albumin from plasma is the "Cohn" cold ethanol procedure [Cohn, et al., J.M. Chem. Soc., 68 pp. 459–475 (1946); see, also, U.S. Pat. No. 2,710,294]. Briefly put, the Cohn process is predicated on selective solubility of proteins under varying conditions of ethanol solvent concentration, protein concentration, temperature, ionic strength and pH. By selective precipitation of proteins from successive supernatants, albumin is eventually isolated in a commercially desirable purified form. See, generally, Kirk-Othmer, "Encyclopedia of Chemical Technology", Vol. 3, pp. 576–600. It is unfortunately the case that successive precipitations in the cold alcohol process will result not only in loss of plasma albumin (and diminution of final yields) but will result also in some degree of destruction of functional or structural characteristics of albumin. Thus, each successive precipitation and resuspension, may enhance the purity, but may also affect the native character of the albumin.

In response to chronic low yield problems in cold alcohol fractionation procedures, the art has developed alternative fractionation processes involving ion exchange chromatography. Solid-liquid column chromatography has classically been a versatile and highly beneficial technique for a fractionation and purification of proteins owing to the high degree of selectivity of ion "exchangers" available. This selectivity, when applied to plasma fractionations directed toward isolation of albumin, has resulted in advantages over prior alcohol treatment processes in terms of both increased purity and yield of albumin. There have been reports, for example, of overall albumin yields from starting plasma on the order of 95% or better, as well as reports of immunoelectrophoretically verified purity for albumin products in excess of 96%. See, e.g., Curling, et al., Vox Sanguinis, 33, No. 2, pp. 97–107 (1977).

While the production of such "chromatographically pure" albumin in high yields constitutes an advance over prior art isolations, the chromatographic procedures reported have not been shown to be significantly less destructive of the native characteristics of the albumin than are the cold alcohol fractionation procedures. It is noteworthy, for example, that known ion exchange chromatographic methods for purification of albumin often involve multiple precipitation and resuspension steps similar to those extant in the cold alcohol fractionation processes and further involve multiple desorbtions of the albumin from the ion exchanger materials. Each such manipulation increases the potential for adverse changes in the native character of the albumin molecules.

There exists, therefore, an ongoing need for new procedures which will efficiently isolate purified albumin from plasma while minimizing potential alterations in the native structure or character of the albumin or other plasma components. A reduction in handling or manipulation, with or without greater yield has obvious advantages in commercial applications as well.

BRIEF SUMMARY

According to the present invention, "chromatographically pure" plasma albumin is obtained in high yields by ion exchange chromatographic procedures which maintain the albumin in a solution phase throughout processing.

In practice of the invention, a cryosupernatant plasma (Cohn fraction II+III S or its equivalent in protein content) is subjected to three distinct processing operations. One operation involves intimately contacting the albumin-containing fluid with a finely divided lipoprotein extractant. A second operation involves treatment of the albumin-containing fluid to adjust the pH to within from about 4.5 to about 4.9 and bringing the fluid into intimate contact with a cationic exchange substance to effect removal of "albumin-contaminating" proteinaceous material having an isoelectric point below that of albumin. A third operation involves treatment of the albumin-containing fluid to effect a pH adjustment to within from about 5.1 to about 5.5 and intimately contacting with an anionic exchange substance to effect removal of "albumin-contaminating" proteinaceous material having an isoelectric point above that of albumin. At no point in the process of the invention is the albumin precipitated or removed from the solution phase. The order of practice of the operations of contracting the albumin-containing fluid with cationic and anionic exchange substances is not critical but it is preferred that practice of the invention involve a treatment of the initial cryosupernatant or its equivalent with the lipoprotein extractant material so that the ion exchangers may additionally act as molecular sieves for removal from the fluid of very fine residual particulate material used as the lipoprotein extractant. The operations may be carried out in batch or continuous processes, directly upon the ethanolic cryosupernatant or upon a supernatant from which ethanol has been removed by gel filtration.

Preferred lipoprotein extractants for use according to the invention include finely divided fume silica such as that available from Degussa, Inc. (Teterboro, N.J.) under the trade designation, "Aerosil 380". Preferred anionic ion exchange substances for use in practice of the invention include commercial substances providing a quarternary amine on a modified dextran or agarose core, e.g., the high porosity, dextran core material available from Pharmacia Fine Chemicals AB (Uppsala, Sweden) under the trade designation, "QAE Sephadex A-50". Preferred cationic ion exchange substances for use in the invention include commercial substances providing a sulfonic acid on a modified dextran or agarose cose, e.g., the high porosity, dextran core material available from Pharmacia Fine Chemicals AB under the trade designation, "SP Sephadex C-50". Commercial anionic and cationic ion exchangers employing an agarose core are available from a variety of sources, including the Marine Colloids Division of FMC Corporation and BioRad Laboratories.

It is immediately apparent that the procedures of the present invention are wholly compatible with existing systems for isolation of other existing protein fractions from plasma. The procedures do not interfere, for example, with those directed toward isolation of gamma globulins because these are preliminarily isolated by withdrawal of the Cohn fraction II+III *precipitate*. In a like manner, proteinaceous materials separated from the albumin-containing fluid by chromatographic procedures may be readily recovered and subjected to further purification by elution from the ion exchanger materials.

Numerous other aspects and advantages of the invention will become apparent to those skilled in the art upon consideration of the following detailed description of preferred embodiments thereof.

DETAILED DESCRIPTION

Cationic and anionic absorptions of the type employed in practice of the present invention are illustrated by the following example of simple batch and column absorptions practiced on a Cohn II+IIIS cryosupernatant including its "native" ethanolic solvent.

EXAMPLE 1

A Cohn II+IIIS cryosupernatant is obtained from plasma by well known techniques. The supernatant solution so obtained has an alcohol concentration of approximately 20%, an ionic strength of ~0.07, a pH of approximately 7.2, and is maintained at a temperature of approximately $-5°$ C. Because anionic and cationic ion exchange chromatographic procedures of the invention are carried out at pH's near the isoelectric point of albumin (pH=pI=5.0) the initial operational steps involve a downward adjustment of pH with dilute mineral (e.g., 1 N hydrochloric or phosphoric) acid. Precipitation of albumin during this adjustment is avoided by reduction of alcohol concentration in the supernatant from 20% to about 10 to 12% by addition of chilled distilled water. The pH adjustment to about 4.7 results in precipitation of an essentially albumin-free protein fraction which may be saved or discarded. The albumin-containing solution is clarified by filtration or centrifugation and to the solution is added about 0.5 g QAE-Sephadex A-50 (in dry powder form with chloride counter ion) per 50 ml. fluid. The suspension of ion exchanger and fluid is maintained by stirring in the cold for from about 2 to 16 hours to effect the removal from the fluid of proteinaceous material having an isoelectric point below that of albumin. The residual, albumin-containing fluid is removed and brought up to original volume with washes from the swelled ion exchanger.

The albumin-containing fluid is then subjected to pH adjustment to about 5.3 through use of dilute (1N) sodium hydroxide. This adjustment is followed by contact with 0.5 g (per 50 ml. fluid) of SP-Sephadex C-50 in the same manner as described for contact with the anionic ion exchanger to effect removal of proteinaceous material having an isoelectric point above that of albumin. The residual fluid and washes from the exchanger substance comprises a substantially pure solution of albumin. The albumin solution may be concentrated and/or subjected to lyophilization to obtain the albumin in dry powder form.

The foregoing batch process may, of course, be performed as a continuous process by serially passing the respective pH-adjusted, albumin-containing fluids through a column containing the appropriate ion exchanger. The particular pH adjustments noted above (respectively, to 4.7 and then 5.3) are, of course, not absolutely fixed. The operative range for use of the anionic ion exchanger according to the invention is any pH below 5.0, the isoelectric point of albumin. Adjustment of the pH to very near 5.0 is likely to result in some degree of albumin binding and an overall lower yield of purified albumin product. Adjustment to below about 4.5, on the other hand, is likely to result in a lesser degree of binding of albumin-contaminating proteins to the ion exchanger and an overall higher yield but higher degree of impurity of the product. An appropriate practical range within which adjustments of fluid pH for anionic ion exchanger treatment may be made is from about 4.5 to about 4.9. For the same reasons, an appropriate practical range for pH adjustments prior to cationic ion exchanger treatment is from about 5.1 to about 5.5.

Salt (NaCl) concentrations for the fluids in batch and continuous processes are maintained at below about 0.070M and preferably at about 0.050 to 0.060M. Recycling of the ion exchangers and/or isolation of protein adsorbed thereon may be accomplished by any of a variety of techniques well known in the art. A suitable eluent for absorbed material on the anionic ion exchanger is 0.1M NaCl or 0.1M $NaH_2PO_4$, and 0.1M $Na_2HPO_4$ is similarly suitable for eluting protein from the cationic ion exchanger. Of course, a series of selective eluents may be employed for the purpose of isolation of individual proteinaceous components bound to the ion exchangers.

The following example illustrates practice of the invention in the isolation of purified albumin from Cohn II+III cryosupernatant from which ethanol is removed. Such ethanol-free methods possess certain substantial advantages over the methods of Example 1 in terms of freedom from the rather rigid low temperature requirements ($-2°$ to $-5°$ C.) for operations on ethanolic systems. The example also illustrates practice of lipoprotein extraction operations which enhance the purity of the final albumin product through removal, e.g., of "contaminating" lipoprotein not readily removed by chromatographic techniques.

EXAMPLE 2

Cohn II+III supernatant is treated to removed alcohol and salt by, for example, gel filtration using commercial gel material such as that available from Pharmacia Fine Chemicals AB under the trade designation "Sephadex G-25" to effect removal of both salts and ethanol. The gel filtration process usually results in a volume expansion of the albumin-containing fluid by 30 to 50%. Well known ultrafiltration processes may be employed to the same effect with or without volume expansion. Salt is added back to a desired concentration of less than 0.070 M and preferably 0.05 to 0.06 M.

The ethanol-free solution is next treated with an extractant for lipoprotein. A preferred material for use in this procedure is finely divided fume silica such as is commercially available from Degussa, Inc., under the trade designation "Aerosol 380". The extraction procedure more specifically involves the slow addition, with stirring or shaking, of from 1 to 10 mg/ml of the silica. Stirring or shaking is continued in the cold (2° to 5° C.)

for from 5 to about 64 hours and preferably from 30 to 64 hours. The suspension is then centrifuged or filtered to yield a fluid substantially free of lipoprotein. The extraction procedure may be carried out over a pH range of from about 4.0 to about 6.5 without loss of albumin from the fluid.

The alcohol-free, lipoprotein-free fluid is then subject to serial anionic and cationic chromatographic procedures as set out in Example 1 to secure a purified albumin. As noted above, the final albumin-containing fluid may be concentrated (after removal of salt by e.g., a further gel filtration with Sephadex G-25) to a final form for therapeutic administration, i.e., to 5% or 25% albumin solutions. Alternatively, the albumin-containing fluid may be subjected to lyophilization processing to yield albumin in a dry form. The former process is, of course, less likely to result in destruction of natural characteristics of the albumin and is consequently more consistent with the aforementioned advantages of the invention in terms of preserving the albumin in a dissolved state throughout the isolation procedure.

EXAMPLE 3

A series of twenty human plasma albumin isolations (including one re-run) were carried out to establish operability of the invention and ascertain the effects upon stability of 5% and 25% albumin solutions of varying durations of lipoprotein extraction operations using the fume silica. Stability is, of course, an indirect measure of freedom from contaminating protein.

All samples were processed generally according to the procedures of Example 2, i.e., the starting material consisted of Cohn II+III cryosupernatant subjected to gel filtration for purposes of alcohol and salt removal; the fluid was then subjected to lipoprotein extraction; the fluid was next serially subjected to anionic and cationic chromatographic treatments (with accompanying pH and salt adjustments); and, finally, 5% and 25% stock solutions were prepared by concentration of the fluid. Table I, below, sets out the results of stability and electrophoretic purity testing. Except where indicated, anionic chromatographic treatment proceded cationic treatment and silica extractions were carried out at 2° to 5° C. Satisfactory or unsatisfactory stability was determined on the basis of relative increases in Nephelometer Units (N.U.) as a function of storage for specified times at elevated temperatures. Increases to not more than 16 N.U. after exposure to 60° C. to 10 hours, and to not more than 21 N.U. after exposure to 57° C. for 50 hours are considered satisfactory.

TABLE I

| Sample No. | Solution Type | Stability N.U. Initial | N.U. 10 Hrs 60° C. | N.U. 50 Hrs 57° C. | Electrophoresis % Albumin | Duration Silica Treatment |
|---|---|---|---|---|---|---|
| 1 | 25% | 3.2 | U* | U | — | 5 Hrs |
| 2 | 5% | 5.4 | 5.4 | 7.3 | — | 5 Hrs |
| 3** | 25% | 2.3 | U | U | — | 5 Hrs |
| 4 | 5% | 2.9 | 7.1 | 6.6 | 98.8% | 5 Hrs |
| 5 | 25% | 4.4 | 11.4 | 19.4 | 97.5% | 16 Hrs |
| 6 | 25% | — | — | U | 97.8% | 24 Hrs |
| 7 | 25% | — | — | U | 97.6% | 24 Hrs |
| 8 | 25% | — | — | U | 97.9% | 24 Hrs |
| 9 | 25% | — | — | U | 97.5% | 24 Hrs |
| 10 | 25% | — | 7.4 | 16.0 | 97.2% | 30 Hrs |
| 11 | 5% | 3.4 | 3.0 | 3.4 | 98.4% | 30 Hrs |
| 12 | 25% | 2.4 | 3.6 | 3.8 | 98.8% | 30 Hrs |
| 13 | 5 | 5.2 | 10.3 | 5.1 | 98.9% | 30 Hrs |
| 14 | 25% | 4.0 | 9.8 | 4.9 | 98.8% | 30 Hrs |
| 15 | 25% | — | 12.0 | 11.6 | 97.6% | 48 Hrs |
| 16 | 5% | 5.3 | 6.5 | 6.9 | 98.7% | 64 Hrs |
| 17 | 5% | 6.0 | 6.2 | 6.7 | 98.6% | 64 Hrs |
| 18 | 5% | 3.3 | 3.8 | 5.8 | 96.9% | 64 Hrs |
| 19 | 25% | 1.9 | 8.9 | U | — | 64 Hrs |
| 19a*** | 25% | 6.2 | 12.2 | 18.9 | 96.9% | 64 Hrs |

*U = Unsatisfactory
**Cationic treatment preceded anionic treatment
***Re-test

As may be ascertained from the data presented in Table I, relatively high purity of albumin is achieved for all of the albumin samples produced. Further, while one of the 5% solutions exhibited satisfactory stability after only 5 hours of lipoprotein extraction with the fume silica, none of the 25% solutions were satisfactorily stable according to the test criteria unless subjected to 30 hours or more of such extraction. It appears quite likely, however, that the duration of effective lipoprotein extraction could be materially shortened by use of a more "continuous" mechanical processing.

Numerous modifications and variations in the above-described, presently-preferred embodiments of the invention are expected to occur to those skilled in the art and therefore only such limitations as appear in the appended claims should be placed thereon.

What is claimed is:

1. In the process for isolation of purified plasma albumin wherein plasma is processed by cold alcohol fractionation to develop an albumin-containing Cohn II+III supernatant fluid, an improvement in the procedure for further isolation of albumin from proteinaceous material in the fluid, said improvement comprising the steps of:
   (a) intimately contacting said fluid with lipoprotein extractant means;
   (b) adjusting the pH of the fluid to from about 4.5 to 4.9 and intimately contacting the pH-adjusted fluid with an anionic ion exchanger means for removing from said ph-adjusted fluid proteinaceous materials having an isoelectric point below that of albumin; and
   (c) adjusting the pH of said to fluid from about 5.1 to 5.5 and intimately contacting the pH-adjusted fluid with a cationic ion exchanger means for removing from said pH-adjusted fluid proteinaceous materials having an isoelectric point above that of albumin,
   whereby an albumin-containing fluid product is obtained substantially free of contaminating proteinaceous materials having an isoelectric point below or above that of albumin.

2. The improvement of claim 1 wherein said steps are performed in consecutive sequence, beginning with step (a), followed by (b), and followed by (c).

3. The improvement of claim 1 wherein said lipoprotein extractant means comprises finely divided fume silica.

4. The improvement of claim 1 wherein said anionic ion exchanger means comprises a modified dextran to which quarternary amine functional groups are attached.

5. The improvement of claim 1 wherein said cationic ion exchanger means comprises a modified dextran to which sulfonic acid functional groups are attached.

6. The improvement of claim 1 further including the step of removing alcohol from said fluid.

7. The improvement of claim 6 wherein said alcohol removal step precedes the operation of any of steps (a), (b), or (c).

8. The improvement of claim 1 wherein said pH adjustment in step (b) comprises adjustment to pH 4.7.

9. The improvement of claim 1 wherein said pH adjustment in step (c) comprises adjustment to pH 5.3.

10. The improvement of claim 1 wherein step (a) is carried out over a period of from 5 to 64 hours.

11. The improvement of claim 1 further including the step of concentrating said fluid product to form a therapeutic albumin solution of desired albumin concentration.

* * * * *

UNITED STATES PATENT AND TRADEMARK OFFICE
CERTIFICATE OF CORRECTION

PATENT NO. : 4,228,154
DATED : October 14, 1980
INVENTOR(S) : JOSEPH D. FISHER ET AL.

It is certified that error appears in the above-identified patent and that said Letters Patent are hereby corrected as shown below:

Col. 1, line 15, "fractionated-" should be --fractionated--.

Col. 1, line 31, "Technology``", should be --Technology''--.

Col. 2, line 39, "contracting" should be --contacting--.

Col. 2, line 64, "cose" should be --core--.

Col. 4, line 50, "removed" should be --remove--.

Col. 4, line 65, "Aerosol 380" should be --Aerosil 380--.

Col. 5, line 42, "proceded" should be --preceded--.

Col. 5, line 48, "to 10 hours" should be --for 10 hours--.

UNITED STATES PATENT AND TRADEMARK OFFICE
CERTIFICATE OF CORRECTION

PATENT NO. : 4,228,154
DATED : October 14, 1980
INVENTOR(S) : JOSEPH D. FISHER ET AL.

It is certified that error appears in the above-identified patent and that said Letters Patent are hereby corrected as shown below:

Col. 5, line 66, Table 1, Sample No. 13, "5" should be --5%--.

Col. 5, line 57, Table 1, Sample No. 1, Duration, "5 Hrs" should be --5 Hrs (15°C)--.

Col. 6, line 48, "of said to fluid", should be --of said fluid--.

Signed and Sealed this

Nineteenth Day of May 1981

[SEAL]

Attest:

RENE D. TEGTMEYER

Attesting Officer

Acting Commissioner of Patents and Trademarks